United States Patent [19]

Blechman et al.

[11] Patent Number: 4,526,539

[45] Date of Patent: Jul. 2, 1985

[54] PALATAL RETENTION DEVICE

[75] Inventors: Abraham Blechman, Tappan, N.Y.; Eugene A. Pescatore, Elmwood Park, N.J.

[73] Assignee: Medical Magnetics, Inc., Ramsey, N.J.

[21] Appl. No.: 584,813

[22] Filed: Feb. 29, 1984

[51] Int. Cl.³ .............................................. A61C 7/00
[52] U.S. Cl. ........................................ 433/18; 433/6; 128/1.3; 128/419 F
[58] Field of Search .......................... 433/6, 7, 18, 189; 128/1.3

[56] References Cited

U.S. PATENT DOCUMENTS 2,732,621  1/1956  Pelzmann ............................. 433/189
3,259,129  7/1966  Tepper .................................... 433/6

Primary Examiner—Robert Peshock
Attorney, Agent, or Firm—Hopgood, Calimafde, Kalil, Blaustein & Judlowe

[57] ABSTRACT

A palatal body is custom configured and dimensioned to fit within the oral cavity with an outer edge conforming to and engaging the lingual faces of the teeth of the maxillary arch. The dimensions are chosen to retain the arch either in an expanded condition associated with separation of the mid-palatal suture, or in some other predetermined position following suitable prior treatment of a cleft palate patient. A plurality of diametrally or longitudinally polarized cylindrical magnets are arrayed in parallel and in parallel to the palate body, all oriented with their axes in the bucco-lingual direction, and individually mounted for rotation under the influence of intraoral activity for inducing therapeutic levels of voltage and current in the adjacent bone structure of the natural palate on either side of the palatal gap.

10 Claims, 7 Drawing Figures

PALATAL RETENTION DEVICE

BACKGROUND OF THE INVENTION

The present invention relates to an orthodontic device for intra-oral placement within the maxillary arch.

Among orthodontic procedures there is that wherein the maxillary arch is subjected to laterally spreading force to establish a split or a resetting of the mid-palatal suture. One such device is described and claimed in our copending patent application Ser. No. 560,878 filed Dec. 13, 1983, and entitled "PALATAL EXPANSION DEVICE." After having expanded the maxillary arch laterally, i.e., along the bucco-lingual axis, it becomes necessary to maintain the maxillary arch in the expanded condition with its separated mid-palatal suture while promoting osteogenesis to close such suture.

Another condition known to orthodontics requiring retention of the maxillary arch while promoting osteogenesis is that associated with therapeutic treatment of cleft palates. In such conditions the naturally occurring gap in the hard palate, usually after appropriate corrective procedures to reshape the maxillary arch and palate structure, is desirably treated to restrain movement while promoting bridging closure of the gap through osteogenic activity.

It is known that osteogenesis can be promoted or stimulated by causing small electric currents to pass through the bone structure bordering a fracture or break, and the present invention seeks to make use of such phenomenon.

SUMMARY OF THE INVENTION

It is, therefore, one object of the present invention to provide an orthodontic device for maintaining a maxillary arch in a buccally expanded condition with a separated mid-palatal suture while promoting osteogenesis to close said mid-palatal suture.

It is another object of the present invention to provide an orthodontic device for inhibiting lingual movement of a maxillary arch bordering a natural palate with a gap therein while promoting osteogenesis to close said palatal gap.

A general object is to meet the above objects with structure which may be worn by the patient with minimum discomfort and for the shortest period of time.

In accordance with the invention there is provided such device comprising a palate body having an outer edge contiguous to and in general conformance with the lingual contouring of the teeth of said maxillary arch, and a plurality of permanent magnets carried by said palate body, said magnets being movable relative to one another and subject to intra-oral lingual activity for developing a fluctuable magnetic flux field adapted to induce mild electric currents in the bone structure of the natural palate on either side of said gap sufficient to promote osteogenesis to close such gap.

BRIEF DESCRIPTION OF THE DRAWINGS

The invention will be better understood after reading the following detailed description of the presently preferred embodiments thereof with reference to the appended drawings in which.

Throughout the figures of the drawings the same reference numerals are used to designate the same or similar parts.

DETAILED DESCRIPTION OF THE PRESENTLY PREFERRED EMBODIMENTS

Figure 1:
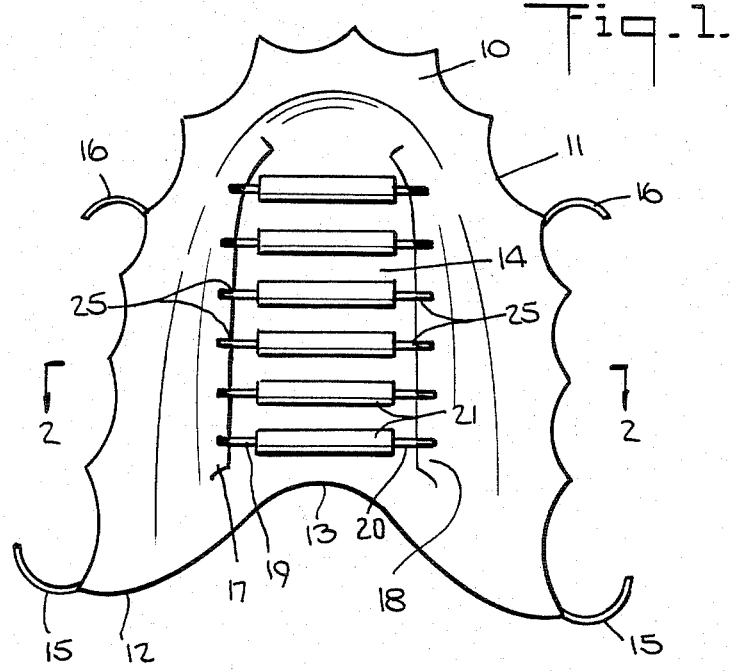
FIG. 1 is a plan view, somewhat exaggerated for clarity, of an orthodontic device embodying the present invention as seen from the side that will face the tongue.
Figure 2:
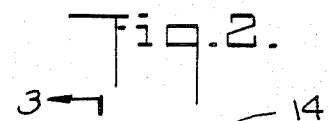
FIG. 2 is a transverse sectional view taken along the line 2—2 of the device in FIG. 1.

Referring to FIGS. 1 and 2 there is shown a palate body 10 having an outer edge 11 in general conformance with the lingual contouring of teeth of the maxillary arch of a patient, a posterior edge 12 with a reentrantly curved portion 13 for accommodating the tongue in the post-dam area, and a medial arched or vault portion 14 for conforming generally to the arched contour of the natural palate. Preferably, the body 10 is made by conventional impression techniques to provide a custom fit to the patient, and is formed from a biocompatible material, e.g., an acrylic resin or a biocompatible non-magnetic stainless steel, or the like. Where a fixed installation is desired anchoring devices may be carried at molar and premolar regions of outer edge 11 for uniting with orthodontic bands. Where a removable appliance is desired, the device can be in the form shown wherein orthodontic clasps 15-16 are provided for removable engagement with corresponding teeth.

While the body 10, as described so far, is capable of maintaining the maxillary arch in a predetermined condition resisting lingual shift, the present invention contemplates shortening the time of treatment by providing for osteogenic stimulation. For this purpose the body 10 is provided within the medial vault portion 14 on the lingual face with a pair of confronting ridges 17-18 into which are journalled the respective arbors 19-20 of a plurality of permanent magnet units 21.

Figure 3:
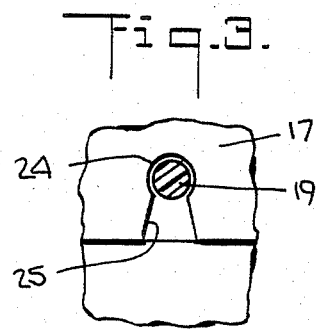
FIG. 3 is a fragmentary sectional view taken along line 3—3 in FIG. 2, showing the mounting arrangement for one of the magnet shafts or arbors.
Figure 4:
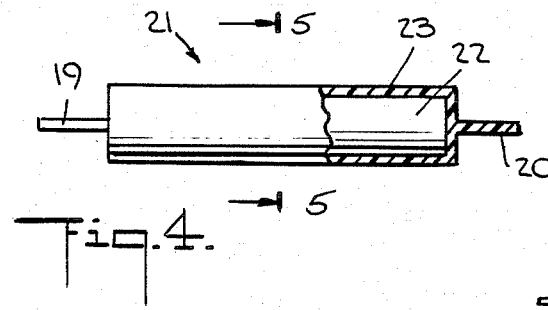
FIG. 4 is a plan view with portions broken away of one of the magnets used in the embodiment of FIGS. 1 and 2, showing the details thereof.
Figure 5:
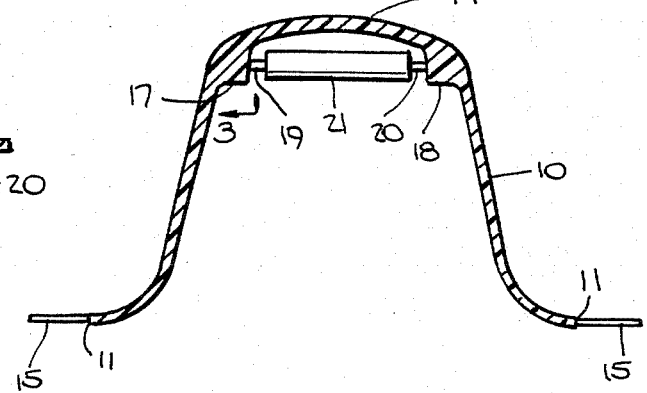
FIG. 5 is a transverse sectional view taken along line 5—5 in FIG. 4.
Figure 5:
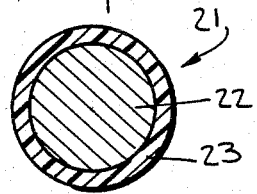

The magnet units are shown in detail in FIGS. 4 and 5 and preferably consist of a circular cylindrical body 22 of magnetic material encased in a biocompatible material 23, which can be the same as or similar to that from which the body 10 is constructed. The arbors 19-20 can be molded or formed at opposite ends integral with the material encasing the magnet. Assembly of the magnet units 21 to the body 10 is facilitated by providing a series of key-hole type slots 24, the details of which are best shown in FIG. 3, with diverging entryways 25 permitting the arbors 19-20 to be snapped through the respective entryways into the circular cavities wherein the arbors are free to rotate. Thus, the parallel array of magnets seen in FIG. 1 are all free to rotate relative to one another and to the body 10 under the random impetus imparted thereto by engagement with the tongue during swallowing, speaking, eating and the like.

Instead of providing snap-in slots or cavities for receiving the arbors 19–20 of the magnet units 21, the latter can be molded or cast directly into the body 10. Employing known techniques involving the coating of the arbors with wax or other suitable release material, the magnet units can be incorporated within the molds or forms, and the acrylic material or the like then can be cast or molded into the desired configuration with the magnet units already in place. When the wax or other release medium is eliminated in known fashion, the arbors of the magnet units will be free to rotate within the cavities formed therearound.

Figure 6:
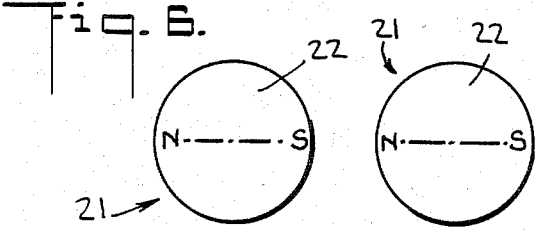
FIG. 6 is a diagrammatic view to indicate the passive orientation of the magnets forming a part of the device of FIG. 1 in accordance with one embodiment thereof.

The magnets 22 are polarized preferably in the diametral direction as shown schematically in FIG. 6. Absent any outside stimulus, the magnets will align with their respective dipoles all facing in the same direction, opposite poles attracting between adjacent units. If an arbitrary plane is selected normal to the longitudinal axes of the units 21 that are in parallel as shown in FIG. 1, the respective dipoles will all be parallel to such common plane. When the subject device is installed in the mouth of a patient the normal intra-oral activity mentioned above will cause the magnet units 21 to rotate in a generally random fashion but sufficiently to cause, as a consequence of variations in or fluctuation of the magnetic flux field, induction of therapeutically beneficial, albeit low-level, voltages and currents in the bone material or structure of the natural palate bordering the now separated mid-palatal suture.

Figure 7:
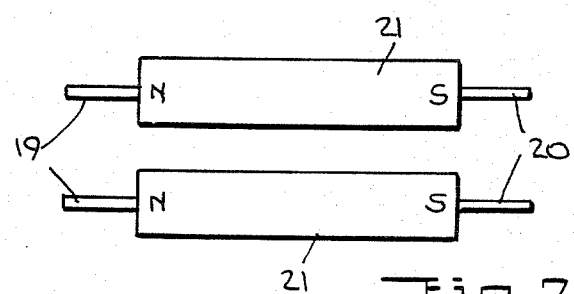
FIG. 7 is a diagrammatic view of two of the magnets showing a modification thereof.

While diametral polarization of the magnets as shown in FIG. 6 is preferred, it is also possible to induce therapeutically sufficient voltages and currents in the bone tissue if the polarization of the magnets is directed in parallel with their long axes as shown in FIG. 7. The effect can be enhanced if the arbors for the magnet units are located slightly off center or eccentric with respect to the longitudinal axis of the cylindrical magnet unit.

Generally speaking, the maximum thickness of the body 10 is about 4 mm, with the thickness being reduced, tapered and faired, as needed, to strike a suitable compromise between that required for therapeutically effective stiffness of the body and patient comfort and tolerance. The protective coating of the magnets assures against incompatibility with body fluids.

Summarizing, the new orthodontic device includes a plurality of the cylindrical magnet units 21 mounted substantially parallel to the palate body 10 by means enabling individual rotation about their respective longitudinal axis. The units 21 are journalled at their respective ends in corresponding supports, the ridges 17–18, on opposite sides of the palate body 10 in the bucco-lingual direction.

While one specific arrangement has been shown and described for mounting the magnet units 21 on the palate body 10, various other arrangements can be used. For example, the ridges 17 and 18 can be omitted and a series of miniature posts or standards provided, molded into the body 10 from the same or different material, each having an aperture for receiving a corresponding arbor 19 or 20.

Having described the invention with reference to the presently preferred embodiments thereof, it is to be understood that numerous changes in construction are contemplated as will occur to those skilled in the subject art without departing from the true spirit of the invention as defined in the appended claims.

What is claimed is:

1. An orthodontic device for inhibiting lingual movement of a maxillary arch bordering a natural palate with a gap therein while promoting osteogenesis to close said palatal gap, comprising a palate body having an outer edge contiguous to and in general conformance with the lingual contouring of the teeth of said maxillary arch, and a plurality of permanent magnets carried by said palate body, said magnets being movable relative to one another and subject to intra-oral lingual activity for developing a fluctuable magnetic flux field adapted to induce mild electric currents in the bone structure of the natural palate on either side of said gap sufficient to promote osteogenesis to close said gap.

2. The orthodontic device of claim 1, in which said permanent magnets each have a circular cylindrical body of magnetic material polarized in the diametral direction, said body being encased in a biocompatible material, and said encased magnet being mounted substantially parallel to said palate body by means enabling rotation about the longitudinal axis of said cylindrical body.

3. The orthodontic device of claim 2, in which said permanent magnets are arrayed with their longitudinal axes generally in parallel.

4. The orthodontic device of claim 3, in which said permanent magnets are each journalled at their respective ends in corresponding supports on opposite sides of said palate body in the bucco-lingual direction.

5. The orthodontic device of claim 2, in which said permanent magnets are journalled at their respective ends in corresponding supports on said palate body.

6. The orthodontic device of claim 1, in which a plurality of orthodontic wires are embedded in said palate body and are exposed along at least part of said outer edge for positive anchorage to corresponding teeth of the maxillary arch.

7. The orthodontic device of claim 1, in which said palate body includes means for outer-edge anchorage to molar and/or premolar teeth.

8. The orthodontic device of claim 1, in which said permanent magnets each have a circular cylindrical body including internal magnetic material and at least an outer layer of a biocompatible material on all exposed surfaces.

9. The orthodontic device of claim 8, in which said permanent magnets are mounted on said palate body by means enabling rotation about the longitudinal axis of said cylindrical body.

10. The orthodontic device of claim 1, in which said permanent magnets are all mounted with their respective dipoles in parallel to a common plane.

* * * * *